United States Patent
Farmer et al.

(10) Patent No.: US 7,374,753 B1
(45) Date of Patent: May 20, 2008

(54) PROBIOTIC LACTIC ACID BACTERIUM TO TREAT BACTERIAL INFECTIONS ASSOCIATED WITH SIDS

(75) Inventors: Sean Farmer, San Diego, CA (US); Robert J. Mikhail, Lakeside, CA (US)

(73) Assignee: Ganeden Biotech, Inc., Mayfield Heights, OH (US)

( * ) Notice: Subject to any disclaimer, the term of this patent is extended or adjusted under 35 U.S.C. 154(b) by 0 days.

(21) Appl. No.: 09/424,527

(22) PCT Filed: Jun. 3, 1998
(Under 37 CFR 1.47)

(86) PCT No.: PCT/US98/11347
§ 371 (c)(1),
(2), (4) Date: May 29, 2003

(87) PCT Pub. No.: WO98/54982
PCT Pub. Date: Dec. 10, 1998

Related U.S. Application Data

(60) Provisional application No. 60/048,452, filed on Jun. 3, 1997.

(51) Int. Cl.
*A01N 63/00* (2006.01)
*C12N 1/20* (2006.01)

(52) U.S. Cl. .................. 424/93.46; 435/252.5; 424/93.1; 426/71

(58) Field of Classification Search ............. 424/93.46; 435/252.5; 514/54, 61
See application file for complete search history.

(56) References Cited

U.S. PATENT DOCUMENTS

| | | | | |
|---|---|---|---|---|
| 5,242,938 A | | 9/1993 | Lam | 514/375 |
| 5,322,777 A | | 6/1994 | Selva et al. | 435/71.3 |
| 5,785,990 A | * | 7/1998 | Langrehr | 424/442 |
| 5,968,569 A | * | 10/1999 | Cavadini et al. | 426/61 |
| 6,156,333 A | * | 12/2000 | Langrehr | 424/442 |
| 6,461,607 B1 | * | 10/2002 | Farmer | 424/93.45 |
| 6,849,256 B1 | * | 2/2005 | Farmer | 424/93.46 |
| 2005/0100535 A1 | * | 5/2005 | Farmer et al. | 424/93.46 |

FOREIGN PATENT DOCUMENTS

| | | |
|---|---|---|
| WO | WO 9115199 A1 * | 10/1991 |
| WO | WO 96/11014 | 4/1996 |

OTHER PUBLICATIONS

Dock, D.B. et al. Biocell. 2004, 28(2), 143-150. ("BioNAN" composition, See p. 145, paragraph 2).*
Naruse and Naruse "ATCC 31284" ATCC Global Bioresource Center, Apr. 25, 2007, <http://www.atcc.org/common/catalog/numSearch/numResults.cfm?atccNum=31284> (B. coagulans Hammer=L. sporogenes).*
Langhendries et al. J. Ped. Gastroent. Nutr.(1995) 21, 177-181.*
Green, A.D., "Minimizing the Risk of SIDS" DrGreene.com, Sep. 2004, ,<http://www.drgreene.com/21_509.html>.*
Lindsay, J.A., *Crit. Rev. Microbiol.*, 22(4):257-277 (1966).
Morris, et al., *Med. Hypotheses*, 22(2):211-222 (1987).
Murrell, et al., *J. Med. Microbiol.*, 39(2):114-127 (1993).
Nakamura, et al., *Intl. J. Systematic Bacteriol.*, No. 1, pp. 63-73 (1988).
Reid, et al., *Clin. Microbiol. Rev.*, 3(4):335-344 (1990).
Supplementary European Search Report for EP 98 92 5189, date of mailing: Jan. 14, 2004.

* cited by examiner

*Primary Examiner*—Sandra E. Saucier
*Assistant Examiner*—Aaron J Kosar
(74) *Attorney, Agent, or Firm*—Mintz, Levin, Cohn, Ferris, Glovsky and Popeo, P.C.; Ingrid A. Beattie

(57) ABSTRACT

Compositions including a non-pathogenic lactic acid-producing bacteria, such as a *Bacillus* species, spores or an extracellular product of *B. coagulans*, formulated for oral administration to the intestinal tract for inhibiting bacterial gastrointestinal infections are described. Methods and systems using the compositions for treating gastrointestinal infections, particularly sudden infant death syndrome (SIDS) are also disclosed.

24 Claims, No Drawings

PROBIOTIC LACTIC ACID BACTERIUM TO TREAT BACTERIAL INFECTIONS ASSOCIATED WITH SIDS

This application is a national stage application filed under 371 based on PCT/US98/11347 filed Jun. 3, 1998, which claims priority to provisional Application 60/048,452, filed Jun. 3, 1997.

TECHNICAL FIELD

This invention relates to utilizing a probiotic organism as a food additive or supplement, and specifically relates to use of *Bacillus coagulans* in food or as a food supplement to prevent Sudden Infant Death Syndrome (SIDS) associated with infant gut microbial infections.

BACKGROUND OF THE INVENTION

Probiotic agents are organisms that confer a benefit when they grow in a particular environment, often by inhibiting the growth of other biological organisms in the same environment. Examples of probiotics include bacteria and bacteriophages which can grow in the intestine, at least temporarily, to displace or destroy pathogens and provide other benefits to the host organism (Salminen et al, *Antonie Van Leeuwenhoek*, 70 (24): 347-358, 1996; Elmer et al, *JAMA*, 275:870-876, 1996; Rafter, Scand. J. Gastroenterol. 30:497-502, 1995; Perdigon et al, *J. Dairy Sci.*, 78:1597-1606, 1995; Gandi, *Townsend Lett. Doctors & Patients*, pp. 108-110, January 1994; Lidbeck et al, *Eur. J. Cancer Prev.* 1:341-353, 1992). Probiotic preparations were systematically evaluated for their effect on health and longevity in the early 1900's (Metchnikoff, E., *Prolongation of Life*, Wilham Heinemann, London, 1910; republished by G.P. Putnam's Sons, New York, N.Y., 1970). Since the discovery and widespread use of antibiotics in about 1950 to treat pathological microbes, the use of probiotics has been limited.

The widespread use of antimicrobial drugs, especially broad spectrum antibiotics, has produced serious consequences. Individuals taking antibiotics often suffer from gastrointestinal upset when beneficial microorganisms in the gut are killed, thus changing the balance of the intestinal flora. This imbalance can result in vitamin deficiencies when vitamin-producing gut bacteria are killed and additional illness if a pathogenic organism overgrows and replaces the beneficial gut microorganisms. In addition, widespread antibiotic use has produced increasing numbers of antibiotic-resistant pathogenic microorganisms, including vancomycin-resistant bacteria. Microorganisms that are resistant to multiple drugs have also developed, often with multiple drug resistance spreading between species, leading to systemic infections that cannot be controlled by use of known antibiotics. Thus, there is a need for preventive and therapeutic agents that can control pathogenic microorganisms without the use of antibiotic chemicals.

Sudden Infant Death Syndrome (SIDS) refers to the sudden and unexpected death of an apparently healthy infant, typically between the ages of three weeks to five months, peaking at about three months of age. Generally, the death is due to cardiorespiratory failure in which the child dies quietly with no symptoms that would indicate grave illness before death, although infections in the few weeks before death have been observed in about 85% of SIDS victims. Although SIDS is a leading cause of infant mortality in the developed countries of the world, its cause is not well understood.

Several researchers have reported that various toxigenic bacteria and their enterotoxins are implicated in the aetiology of SIDS (Amon S. S. et al., *Lancet* 1: 1273-1277, 1978; Gurwith M. J. et al., *Am. J. Dis. Child.* 135:1104-1106, 1981; Cooperstock M. S. et al., *Pediatr.* 70:91-95, 1982; Donta S. & Myers M., *J. Pediatr.* 100:431-434, 1982; Amon S. S. et al., *J. Pediat.* 104(1):34-40, 1984; Murrell T. G. et al., *Med. Hypoth.* 22:401-413, 1987; Blackwell C. C. et al., *J. Clin. Pathol.* 45(11 Suppl.):20-24, 1992; Lindsay J. A. et al., *Curr. Microbiol.* 27:51-59, 1993; Murrell W. G. et al., *J. Med. Microbiol.* 39(2):114-127, 1993; Mach A. S. & Lindsay J. A., *Curr. Microbiol.* 28:261-267, 1994; Siarakas S. et al., *Toxicon* 33(5):635-649, 1995). Bacterial species implicated in SIDS include *Clostridium perfringens, C. difficile, C. botulinum, Staphylococcus aureus* and *Escherichia coli*, although the correlation between the presence of particular bacterial species and SIDS has not been entirely consistent between studies (Gurwith M. J. et al., *Am. J. Dis. Child* 135:1104-1106, 1981; Blackwell C. C. et al., *J. Clin. Pathol.* 45(11 Suppl.):20-24, 1992; Murrell W. G. et al., *J. Med. Microbiol.* 39(2):114-127, 1993; Lindsay J. A. et al., *Curr. Microbiol.* 27:51-59, 1993; Siarakas S. et al., *Toxicon* 33(5): 635-649, 1995). *Clostridium* species, particularly *C. perfringens* and *C. difficile*, are most often associated with fecal samples obtained from children who have died of SIDS. Bacterial toxins found in fecal matter and serum of SIDS babies may be etiological agents of SIDS. These bacterial toxins include *C. perfringens* enterotoxin and alpha-toxin, *Staphylococcus* enterotoxin B, *E. coli* heat-stable toxin (STa), *C. difficile* toxins A and B, and *C. botulinum* toxin (Blackwell C. C. et al., *J. Cliff. Pathol.* 45(11 Suppl.):20-24, 1992; Murrell W. G. et al., *J. Med. Microbiol.* 39(2):114-127, 1993; Siarakas S. et al., *Toxicon* 33(5):635-649, 1995). *C. perfringens* Type A enterotoxin has been particularly implicated because of its ability to modulate cytokine production by human animal cells (Lindsay J. A., *Crit. Rev. Microbiol.* 22(4):257-277, 1996). Some of these toxins act synergistically (Siarakas S. et al., *Toxicon* 33(5):635-649, 1995). In animals, *C. perfringens* is responsible for death of several young species (e.g., lamb, pony) and *C. difficile* causes pseudomembranous colitis (Murrell T. G. C. et al. *Med. Hypotheses* 22:401-413, 1987; Murrell W. G. et al, *J. Med. Microbiol.* 39:114-127, 1993).

Although different hypotheses have been offered to explain how these bacteria and/or bacterial toxins may cause or contribute to SIDS, it is generally thought that SIDS results from a series of events in which pathogenic bacteria enter the gut, colonize and produce cytotoxin that initiates a cascade of reactions that lead to silent death (Lindsay J. A., *Crit. Rev. Microbiol.* 22(4):257-277, 1996; Murrell W. G. et al., *J. Med. Microbiol.* 39:114-127, 1993). The cytotoxin may damage intestinal tissue resulting in more efficient systemic absorption of the enterotoxin, without systemic migration of the bacteria. Moreover, intestinal injury may result in increased production of cytokines (e.g., interferon-gamma, tumor necrosis factor and interleukins) that exacerbate the effects of the toxins leading to a biochemical cascade that alters the circuits that control cardiorespiration, leading to irreversible shock and death (Lindsay J. A. et al., *Curr. Microbiol.* 27:51-59, 1993; Mach AS. & Lindsay J. A., *Curr. Microbiol.* 28:261-267, 1994). For example, toxin-induced changes in cell membrane permeability leading to abnormal levels of intracellular ions (potassium and/or calcium) in heart tissue may lead to cardiac failure. These explanations for SIDS are consistent with other studies that have shown an association between intestinal injury and the development of a septic state and distant organ failure in the absence of systemic bacterial infection (Deitch E. A. et al., *Shock* 1(2): 141-145, 1994).

Because SIDS occurs generally in young infants, before the immune system as fully developed, a vaccine against bacterial pathogens associated with SIDS would usually not be effective to prevent SIDS-associated infections because the infant would not produce a sufficient immune response to the immunogen. Anti-toxin antibodies (e.g., as disclosed in U.S. Pat. No. 5,599,539) have limited efficacy because they do not limit growth of the toxin-producing bacteria which can continue to produce toxin and the antibodies may produce an allergic reaction when orally administered. Thus, there is a need for preventive and therapeutic agents that can control the growth of SIDS-associated pathogenic microorganisms, without the use of antibiotics that can affect the beneficial microflora of the infant's gut or contribute to development of microbial drug resistance. Probiotics, which can be taken internally because they are generally regarded as safe, can be used replace or preclude growth of gut pathogens associated with SIDS. Moreover, because of their mode of action, probiotics do not produce antibiotic side effects or lead to drug-resistant pathogens.

Lactic acid producing bacteria (e.g., *Bacillus, Lactobacillus* and *Streptococcus* species) have been used as food additives and there have been some claims that they provide nutritional and therapeutic value (Gorbach S. L., *Ann. Med.* 22(1):37-41, 1990; Reid, G. et al., *Clint. Microbiol. Rev.* 3(4):335-344, 1990). Some lactic acid producing bacteria (e.g., those used to make yogurt) have been suggested to have antimutagenic and anticarcinogenic properties useful for preventing human tumors (Pool-Zobel B. L. et al., *Nutr. Cancer* 20(3):261-270, 1993; U.S. Pat. No. 4,347,240). Some lactic acid producing bacteria also produce bacteriocins which are inhibitory metabolites responsible for the bacteria's antimicrobial effects (Klaenhammer T. R., *FEMS Microbiol. Rev.* 12(1-3):39-85, 1993; Barefoot S. F. & Nettles C. G., *J. Dairy Sci.* 76(8):2366-2379, 1993).

The therapeutic use of probiotic bacteria, especially *Lactobacillus* strains, that colonize the gut has been previously disclosed (Winberg et al, *Pediatr. Nephrol.* 7:509-514, 1993; Malin et al, *Ann. Nutr. Metab.* 40:137-145, 1996; and U.S. Pat. No. 5,176,911).

Selected *Lactobacillus* strains that produce antibiotics have been disclosed as effective for treatment of infections, sinusitis, hemorrhoids, dental inflammations, and other inflammatory conditions (U.S. Pat. No. 4,314,995). *L. reuteri* produces antibiotics with activity against Gram negative and Gram positive bacteria, yeast and a protozoan (U.S. Pat. No. 5,413,960 and U.S. Pat. No. 5,439,678). *L. casei* ssp. *rhamnosus* strain LC-705, DSM 7061, alone or in combination with a *Propionibacterium* species, in a fermentation broth has been shown to inhibit yeast and molds in food and silage (U.S. Pat. No. 5,378,458). Also, antifungal *Serratia* species have been added to animal forage and/or silage to preserve the animal feedstuffs, particularly *S. rubidaea* FB299, alone or combined with an antifungal *B. subtilis* (strain FB260) (U.S. Pat. No. 5,371,011).

*Bacillus coagulans* is a non-pathogenic gram positive spore-forming bacteria that produces L(+) lactic acid (dextrorotatory) in homofermentation conditions. It has been isolated from natural sources, such as heat-treated soil samples inoculated into nutrient medium (*Bergey's Manual of Systemic Bacteriology*, Vol. 2, Sneath, P. H. A. et al., eds., Williams & Wilkins, Baltimore, Md., 1986). Purified *B. coagulans* strains have served as a source of enzymes including endonucleases (e.g., U.S. Pat. No. 5,200,336), amylase (U.S. Pat. No. 4,980,180), lactase (U.S. Pat. No. 4,323,651) and cyclo-malto-dextrin glucano-transferase (U.S. Pat. No. 5,102,800). *B. coagulans* has been used to produce lactic acid (U.S. Pat. No. 5,079,164). A strain of *B. coagulates* (referred to as *L. sporogenes* Sakaguti & Nakayama (ATCC 31284)) has been combined with other lactic acid producing bacteria and *B. natto* to produce a fermented food product from steamed soybeans (U.S. Pat. No. 4,110,477). *B. coagulans* strains have also been used as animal feed additives for poultry and livestock to reduce disease and improve feed utilization and, therefore, to increase growth rate in the animals (International PCT Pat. Applications No. WO 9314187 and No. WO 9411492).

SUMMARY OF THE INVENTION

It has now been discovered that lactic acid bacteria possess the ability to exhibit probiotic activity in preventing gastrointestinal bacterial infections, particularly Sudden Infant Death Syndrome (SIDS). Non-pathogenic lactic acid bacteria are preferably used, with spore-forming *Bacillus* species, particularly *B. coagulans*, being a preferred embodiment. The invention describes therapeutic compositions, therapeutic systems, and methods of use for treating and/or preventing various bacterial gastrointestinal infections, particularly infections associated with SIDS.

According to one aspect of the invention, there is provided a composition comprising viable non-pathogenic lactic acid bacterium in a pharmaceutically acceptable carrier suitable for oral administration to the digestive tract of a human. In one embodiment, a *Bacillus coagulans* strain is included in the composition in the form of spores. In another embodiment, a *Bacillus coagulans* strain is included in the composition in the form of a dried cell mass. In one embodiment, the *Bacillus coagulans* strain is present in the composition at a concentration of $10^3$-$10^{12}$ colony forming units/g, whereas in other preferred embodiments the concentrations are 109-$10^{13}$ colony forming units/g, $10^5$-$10^7$ colony forming units/g, or $10^8$-$10^9$ colony forming units/g. In one embodiment, the *Bacillus coagulans* strain is in a pharmaceutically acceptable carrier suitable for oral administration to a human infant, preferably, a powdered food supplement, a infant formula or an oral electrolyte maintenance formulation.

In another aspect of the invention, there is provided a composition comprising an extracellular product of a *Bacillus coagulans* strain in a pharmaceutically acceptable carrier suitable for oral administration to a human. In one embodiment, the extracellular product is a supernatant or filtrate of a culture of an isolated *Bacillus coagulans* strain.

Another aspect of the invention is a method of preventing or treating a bacterial gastrointestinal infection in a human, comprising the steps of orally administering to a human subject a food or drink formulation containing viable colony forming units of a non-pathogenic lactic acid bacterium, preferably a *Bacillus* species and more preferably an isolated *Bacillus coagulans* strain, and allowing the bacteria to grow in the human subject's gastrointestinal tract. In one embodiment, the human subject is an infant at risk for Sudden Infant Death Syndrome. In another embodiment, the viable colony forming units are spores of *Bacillus coagulans*.

In one embodiment of the method, the step of allowing the non-pathogenic bacteria to grow further includes inhibiting growth of *Staphylococcus* species, *Streptococcus species, Pseudomonas species, Escherichia coli, Gardnerella vaginalis, Propionibacterium acnes, Aeromonas hydrophilia, Aspergillus* species, *Proteus* species, *Aeromonas* species,

*Clostridium* species, *Klebsiella* species, *Canidida* species and *Trichophyton* species. In a preferred embodiment, the method inhibits *Staphylococcus aureus, Staphylococcus pyrogenes, Clostridium perfringens, C difficile, C. botulimum, C. tributrycum, C. sporogenes*, or combinations thereof.

One aspect of the invention is a probiotic composition comprising an isolated *Bacillus* species strain, combined with a pharmaceutically acceptable carrier suitable for oral administration to a human infant, wherein the isolated *Bacillus* species strain is capable of growing at temperatures of about 30° C. to about 65° C., produces L(+) dextrorotatory lactic acid, produces spores resistant to heat up to 90° C., and exhibits probiotic activity that inhibits growth of bacteria associated with Sudden Infant Death Syndrome. In one embodiment, the bacteria associated with Sudden Infant Death Syndrome are *Staphylococcus aureus* and *Clostridium* species. In another embodiment, the probiotic activity results from vegetative growth of the isolated *Bacillus* species strain in the gastrointestinal tract of a human infant. In yet another embodiment, the probiotic activity results from an extracellular product of the isolated *Bacillus* species strain produced in the gastrointestinal tract of a human infant.

The invention also describes a therapeutic system for treating, reducing or controlling gastrointestinal bacterial infections, particularly infections associated with SIDS, comprising a container comprising a label and a therapeutic composition as described herein, wherein said label comprises instructions for use of the composition for treating infection.

The invention provides several advantages. In particular, insofar as there is a detrimental effect to the use of antibiotics because of the potential to produce antibiotic-resistant microbial species, it is desirable to have an antimicrobial therapy which does not utilize conventional antimicrobial reagents. The present invention does not contribute to the production of future generation of antibiotic resistant pathogens.

It should be understood that both the foregoing general description and the following detailed description are exemplary and explanatory only and are not restrictive of the invention as claimed.

DETAILED DESCRIPTION OF THE INVENTION

The present invention is directed to the discovery that lactic acid bacteria, particularly *Bacillus* species, can be used in therapeutic compositions as a probiotic for preventing or controlling gastrointestinal bacterial infections. As discussed further, the compositions can be formulated in many configurations because the bacterium is presented as a viable organism, e.g., as a vegetative cell or as a spore depending on the species and form of probiotic organism, and colonize tissues of the gastrointestinal tract. The cells/spores can be presented in a variety of compositions suited for oral administration to the gastrointestinal tract, directed at the objective of introducing the bacteria to tissues of the gastrointestinal tract.

As used herein, "probiotic" refers to bacteria that form at least a part of the transient or endogenous flora and thereby exhibit a beneficial prophylactic and/or therapeutic effect on the host organism. Probiotics are generally known to be safe by those skilled in the art. Although not wishing to be bound by any particular mechanism, the prophylactic and/or therapeutic effect of a lactic acid bacterium of this invention results from competitive inhibition of growth of pathogens due to superior colonization, parasitism of undesirable microorganisms, lactic acid production and/or other extracellular products having antimicrobial activity, or combinations thereof. These products and activities of a lactic acid bacterium of this invention act synergistically to produce the beneficial probiotic effect.

A lactic acid bacterium suitable for use in the methods and compositions of the invention, as defined for use in the present invention, produces L(+) lactic acid, and does not substantially produce D(−) lactic acid. There are many L(+) lactic acid producing bacteria currently identified as described herein. The property of L(+) lactic acid production is key to the effectiveness of the probiotic lactic acid producing bacteria of this invention because the acid production increases acidity in the local microfloral environment, which does not support growth of deleterious and undesirable bacteria. By the mechanism of lactic acid production, the probiotic inhibits growth of competing and deleterious bacteria. In addition, whereas L(+) lactic acid is absorbed and metabolised in the glycogen synthesis pathway, D(−) lactic acid is metabolised very slowly, and can lead to metabolic disturbances such as acidosis.

Typical lactic acid producing bacteria useful as a probiotic of this invention which are L(+) lactic acid producers include *Lactobacillus acidophilus, L. salivarius, L. g.g., L. plantenim, L. delbnikeii, L. sporegenes* (aka *B. coagulans*), *L. rhamnosus, L. casei, Bifidobacterium longum, B. bifidum, B. infantus, Bacillus* species, and the like.

There are several *Bacillus* species particularly useful according to the present invention, including *Bacillus coagulans, Bacillus subtilis, Bacillus laterosporus* and *Bacillus laevolacticus*. Although exemplary of the invention, *Bacillus coagulans* is only a model for the other lactic acid producing species of probiotic bacteria useful in the invention, and therefore the invention is not to be considered as limiting and it is intended that any of the lactic acid producing species of probiotic bacteria can be used in the compositions, therapeutic systems and methods of the present invention.

A *Bacillus* species is particularly suited for the present invention due to the properties in common between species of the *Bacillus* genus, including in particular the ability to form spores which are relatively resistant to heat and other conditions, making them ideal for storage (shelf-life) in product formulations, and ideal for survival and colonization of tissues under conditions of pH, salinity, and the like on tissues subjected to microbial infection. Additional useful properties include non-pathogenic, aerobic, facultative and heterotrophic, rendering these species safe, and able to colonize gastrointestinal tissue, including intestinal villi.

Because *Bacillus* spores are heat-resistant and additionally can be stored as a dry power, they are particularly useful as a prophylactic or for treatment of infection by bacteria associated with SIDS by including the spores in infant formula, infant foods and food supplements, infant rehydration and electrolyte maintenance compositions and the like, which are generally rehydrated and heated before feeding them to an infant. These pressure-resistant spores are also suitable for use in pressure-treated compositions such as pressed wafers and chewable tablets.

It will be appreciated that *B. coagulans* is also useful as a probiotic gastrointestinal treatment for children over the age of one year who exhibit symptoms of gastrointestinal infection or adults at risk of complications from intestinal infections (e.g., the elderly or immunocompromised individuals). For older children and adults, *B. coagulans* is orally administered as a food supplement mixed with food or drinks, a pressed wafer or chewable tablet or similar well-known compositions suitable for oral administration.

One aspect of the invention thus relates to inhibition of growth of SIDS-associated bacteria in an infant. This inhibition has value in promoting a healthy population of intestinal flora, whether or not the inhibited organisms are ultimately the cause of SIDS.

There are a variety of different *Bacillus* species useful in the present invention, including, but not limited to many different strains available through commercial and public sources, such as the American Tissue Culture Collection (ATCC). For example, *Bacillus coagulans* strains are available as ATCC Accession Numbers 15949, 8038, 35670, 11369, 23498, 51232, 11014, 31284, 12245, 10545 and 7050. *Bacillus subtilis* strains are available as ATCC Accession Numbers 10783, 15818, 15819, 27505, 13542, 15575, 33234, 9943, 6051a, 25369, 11838, 15811, 27370, 7003, 15563, 4944, 27689, 43223, 55033, 49822, 15561, 15562, 49760, 13933, 29056, 6537, 21359, 21360, 7067, 21394, 15244, 7060, 14593, 9799, 31002, 31003, 31004, 7480, 9858, 13407, 21554, 21555, 27328 and 31524. *Bacillus laterosporus* strains are available as ATCC Accession Numbers 6456, 6457, 29653, 9141, 533694, 31932 and 64, including *Bacillus laterosporus* BOD. *Bacillus laevolacticus* strains are available as ATCC Accession Numbers 23495, 23493, 23494, 23549 and 23492.

The growth of these various *Bacillus* species to form cell cultures, cell pastes and spore preparations is generally well known in the art. Exemplary culture and preparative methods are described herein for *Bacillus coagulans* and can readily be used and/or modified for growth of the other lactic acid producing bacteria of this invention.

Exemplary methods and compositions are described herein using *Bacillus* coagulates as a probiotic for controlling, treating or reducing gastrointestinal bacterial infections.

A. *Bacillus coagulans* Compositions

The present invention describes the use of purified *Bacillus coagulans* as an exemplary and preferred probiotic for biological control of various bacterial infections in the intestinal tract.

Because *B. coagulans* forms heat-resistant spores, this species is particularly useful for making pharmaceutical compositions for treating microbial infections. Formulations that include viable *B. coagulans* spores cells in a pharmaceutically acceptable carrier are particularly preferred for making and using both preventive and therapeutic compositions.

*B. coagulans* is non-pathogenic and is generally regarded as safe (i.e., GRAS classification by the U.S. Food and Drug Administration). The Gram positive rods have a cell diameter of greater than 1.0 μm with variable swelling of the sporangium, without parasporal crystal production.

1. Growth of *B. coagulans*

*B. coagulans* is aerobic and facultative, grown typically in nutrient broth, pH 5.7 to 6.8, containing up to 2% (by wt) NaCl, although neither NaCl nor KCl are required for growth. A pH of about 4 to about 6 is optimum for initiation of growth from spores. It is optimally grown at about 30° C. to about 55° C., and the spores can withstand pasteurization. It exhibits facultative and heterotrophic growth by utilizing a nitrate or sulphate source. Additional metabolic characteristics of *B. coagulans* are summarized in Table 1.

TABLE 1

| Characteristic | *B. coagulans* Response |
| --- | --- |
| Catalase production | Yes |
| Acid from D-Glucose | Yes |
| Acid from L-Arabinose | Variable |
| Acid from D-Xylose | Variable |
| Acid from D-Mannitol | Variable |
| Gas from Glucose | Yes |
| Hydrolysis of Casein | Variable |
| Hydrolysis of Gelatin | No |
| Hydrolysis of Starch | Yes |
| Utilization of Citrate | Variable |
| Utilization of Propionate | No |
| Degradation of Tyrosine | No |
| Degradation of Phenylalanine | No |
| Nitrate reduced to Nitrite | Variable |
| Allatoin or Urate Required | No |

*B. coagulans* can be grown in a variety of media, although it has been found that certain growth conditions produce a culture which yields a high level of sporulation. For example, sporulation is enhanced if the culture medium includes 10 milligrams per liter of manganese sulfate, yielding a ratio of spores to vegetative cells of about 80:20. In addition, certain growth conditions produce a bacterial spore which contains a spectrum of metabolic enzymes particularly suited for the present invention, i.e., control of microbial infections. Although spores produced by these particular growth conditions are preferred, spores produced by any compatible growth conditions are suitable for producing a *B. coagulans* useful in the present invention.

Suitable media for growth of *B. coagulans* include Nutristart 701, PDB (potato dextrose broth), TSB (tryptic soy broth) and NB (nutrient broth), all well known and available from a variety of sources. Media supplements containing enzymatic digests of poultry and fish tissue, and containing food yeast are particularly preferred. A preferred supplement produces a media containing at least 60% protein, and about 20% complex carbohydrates and 6% lipids. Media can be obtained from a variety of commercial sources, notably DIFCO (Detroit, Mich.), Oxoid (Newark, N.J.), BBL (Cockeyesville, Md.) and Troy Biologicals (Troy, Mich.).

A preferred procedure for preparation of *B. coagulans* is described in the Examples.

2. Extracellular Products Having Antimicrobial Activity

*B. coagulans* cultures contain secreted products which have antimicrobial activity. These secreted products are useful in therapeutic compositions according to the present invention. Cell cultures are harvested as described above, and the culture supernatants are collected, by filtration or centrifugation, or both, and the resulting supernatant contains antimicrobial activity useful in a therapeutic composition. The preparation of a *B. coagulans* extracellular product is described in the Examples.

Extracellular products of *B. coagulans* may be included in compositions such as foods and liquids to be fed to infants.

3. Sources of *B. coagulans*

Purified *B. coagulans* bacteria are available from the American Type Culture Collection (Rockville, Md.) using the following accession numbers: *B. coagulans* Hammer NRS T27 (ATCC# 11014), *B. coagulans* Hammer strain C (ATCC# 11369), *B. coagulans* Hammer (ATCC# 31284), and *B. coagulans* Hammer NCA 4259 (ATCC# 15949). Purified *B. coagulans* bacteria are also available from the Deutsche Sammlung von Mikroorganismen und Zellkuturen GmbH (Braunschweig, Germany) using the following accession numbers: *B. coagulans* Hammer 1915$^{AL}$ (DSM# 2356), *B. coagulans* Hammer 1915$^{AL}$ (DSM# 2383, corresponds to ATCC# 11014), *B. coagulans* Hammer$^{AL}$ (DSM# 2384, corresponds to ATCC# 11369), and *B. coagulans* Hammer$^{AL}$ (DSM# 2385, corresponds to ATCC# 15949). *B. coagulans* bacteria can also be obtained from commercial suppliers such as Sabinsa Corporation (Piscataway, N.J.).

These *B. coagulans* strains and their growth requirements have been described previously (Baker et al, *Can. J. Microbiol.* 6:557-563, 1960; Blumenstock, "*Bacillus coagulans* Hammer 1915 und andere thermophile oder mesophile, säuretolerante *Bacillus*-Arten-eine taxonomische Untersuchung", Doctoral thesis, Univ. Göttingen, 1984; Nakamura et al, *Int. J. Syst. Bacteriol.*, 38:63-73, 1988). Strains of *B. coagulans* can also be isolated from natural sources (e.g., heat-treated soil samples) using well known procedures (*Bergey's Manual of Systemic Bacteriology*, Vol. 2, p. 1117, Sneath, P. H. A. et al., eds., Williams & Wilkins, Baltimore, Md., 1986). The results described herein were obtained with *B. coagulans* Hammer obtained from the American Type Culture Collection (ATCC# 31284) which was grown as described herein and stored in lyophilized aliquots at −20° C. All *B. coagulans* that exhibit the properties described herein are considered equivalents of this strain.

*B. coagulans* had previously been mischaracterized as a *Lactobacillus* in view of the fact that as originally described, this bacterium was labeled as *Lactobacillus* sporogenes (See Nakamura et al, cited above). However, this was incorrect because the bacterium of this invention produces spores and through metabolism excretes L(+)-lactic acid, both aspects which provide key features to its utility. Instead, these developmental and metabolic aspects required that the bacterium be classified as a lactic acid *Bacillus*, and therefore it was renamed.

4. Probiotic Antimicrobial Activity of *B. coagulans*

Pathogenic enteric bacteria inhibited by *B. coagulans* activity include *Staphylococcus aureus*, *S. epidermidis*, *Streptococcus pyogenes*, *S.* spp., *Pseudomonas aeruginosa*, *Escherichia coli* (enterohemorragic species), *Clostridium* species including *C. perfingens*, *C. difficile*, *C. difficile*, *C. botulinum*, *C. tributrycum*, and *C. sporogenes*, *Gardnerella vaginalis*, *Propionibacterium acnes*, *Aeromonas hydrophilia*, *Aspergillus* species, *Proteus* species and *Klebsiella* species. These pathogens can cause a variety of gastrointestinal disorders, including SIDS, and the like conditions as are well known in the art. Therefore, use of compositions containing a probiotic that inhibits these pathogens are useful in preventing or treating conditions associated with infection by these pathogens.

Although *B. coagulans* is exemplary, by virtue of the common properties of the lactic acid producing bacteria, a therapeutic composition comprising a lactic acid bacterium of this invention can be used against many of the above-described pathogens. In addition, it is contemplated that the present therapeutic compositions can be used, when formulated for oral administration to the intestinal tissue, to treat infections by bacteria associated with SIDS.

B. Bifidogenic Oligosaccharides

Bifidogenic oligosaccharides, as used in the context of the present invention, are a class of sugars particularly useful for preferentially promoting the growth of a lactic acid bacteria of this invention. These oligosaccharides include fructo-oligosaccharides (FOS), gluco-oligosaccharides (GOS), and other long-chain oligosaccharide polymers that are not readily digested by pathogenic bacteria. The preferential growth is promoted due to the nutrient requirements of this class of lactic acid bacterium as compared to pathogenic bacteria. Bifidogenic oligosaccharides are long chain polymers that are utilized almost exclusively by the indigenous Bifidobacteria and *Lactobacillus* in the intestinal tract and can be similarly utilized by *Bacillus*. Deleterious bacteria such as *Clostridium, Staphylococcus, Salmonella* and *E. Coli* cannot metabolize FOS or other bifidogenic oligosaccharides, and therefor use of these bifidogenic oligosaccharides in combination with a lactic acid bacteria of this invention, particularly *Bacillus*, allows the beneficial and probiotic bacteria to grow and to replace any undesirable or pathogenic microorganisms.

The use of bifidogenic oligosaccharides in therapeutic compositions of the present invention provides a synergistic effect thereby increasing the effectiveness of the probiotic-containing compositions of this invention. This synergy is manifest at least by increasing the ability of the bacterium to grow by increasing the food supplement for probiotic bacteria which preferentially selects for growth of the probiotic bacteria over many other bacterial species in the infected tissue. Thus, the presence of the bifidogenic oligosaccharides in the formulation allows for more effective microbial inhibition by increasing the ability of the probiotic bacteria to grow and therefore provide its benefit.

The bifidogenic oligosaccharide can be used either alone or in combination with a lactic acid bacterium in a therapeutic composition. That is, due to the growth promoting activity of bifidogenic oligosaccharides, the invention contemplates a composition comprising a bifidogenic oligosaccharide of this invention in a lactic acid bacterium growth-promoting amount. As shown herein, these amounts can vary widely since the probiotic will respond to any metabolic amount of nutrient oligosaccharide, and therefore the invention need not be so limited.

A preferred and exemplary bifidogenic oligosaccharide is FOS, although the other sugars can also be utilized, either alone or in combination.

FOS can be obtained from a variety of natural sources, including commercial suppliers. As a product isolated from natural sources, the components can vary widely and still provide the beneficial agent, namely FOS. FOS typically has a polymer chain length of from about 4 to 200 sugar units, with the longer lengths being preferred. For example, the degree of purity can vary widely so long as functional FOS is present in the formulation. Preferred FOS formulations contain at least 50% by weight of fructooligosaccharides compared to simple (mono or disaccharide) sugars such as glucose, fructose or sucrose, preferably at least 80% fructooligosaccharides, more preferably at least 90% and most preferably at least 95% fructooligosaccharides. Sugar content and composition can be determined by any of a variety of complex carbohydrate analytical detection methods as is well known.

Preferred sources of FOS include inulin, Frutafit IQ™ from Imperial Suiker Unie (Sugar Land, Tex.), NutraFlora™ from Americal Ingredients, Inc., (Anaheim, Calif.), Fab-rchem, Inc., (Fairfield, Conn.), and Fruittrimfat Replacers and Sweeteners (Emeryville, Calif.). Bifidogenic oligosaccharides such as GOS, and other long chain oligosaccharides are also available from commercial vendors.

C. Therapeutic Compositions

Compositions of this invention suitable for use in preventing, treating or controlling gastrointestinal bacterial infections, particularly infant bacterial infections, by organisms capable of producing enterotoxin and infections associated with SIDS include live probiotic lactic acid producing bacteria according to the present invention, provided in the form of colony forming units (CFU's) of vegetative cells and/or spores, extracellular antibiotic metabolites of *B. coagulans*, or combinations thereof.

The active ingredients, i.e., live bacteria or extracellular components, comprise about 0.1% to about 50% by weight of the final composition, preferably 1% to 10% by weight, in a formulation suitable for use in making infant formula, added to food, or used directly as a food supplement for infants (e.g. as a powder mixed with infant formula or in a flavored buffered solution administered with a dropper applicator, similar to that used for liquid infant vitamins).

The formulation for a therapeutic composition of this invention may include other probiotic agents or nutrients for promoting spore germination and/or bacterial growth. A particularly preferred material is a bifidogenic factor which promotes growth of beneficial probiotic bacteria as described herein. The compositions may also include known antimicrobial agents, known antiviral agents, known antifungal agents, all of which must be compatible with maintaining viability of the *Bacillus* active agent when *Bacillus* organisms or spores are the active agent. The other agents in the compositions can be either synergists or active agents. Preferably, the known antimicrobial, antiviral and/or antifungal agents are probiotic agents compatible with *Bacillus*. The compositions may also include known antioxidants, buffering agents, and other agents such as coloring agents, flavorings, vitamins or minerals. Thickening agents may be added to the compositions such as polyvinylpyrrolidone, polyethylene glycol or carboxymethylcellulose.

Preferred additional components of a therapeutic composition of this invention can include assorted colorings or flavorings well known in the art, vitamins, fiber, enzymes and other nutrients. Preferred vitamins include vitamins B, C, D, E, folic acid, K, niacin, and the like vitamins. Preferred sources of fiber include any of a variety of sources of fiber including psyllium, rice bran, oat bran, corn bran, wheat bran, fruit fiber and the like fibers. Dietary or supplementary enzymes such as lactase, amylase, glucanase, catalase, and the like enzymes can also be included.

Exemplary vitamins are used in the composition as follows: choline (160 mg/lb), B-6 (10 mg/lb), B-12 (2 ug/lb), niacin (120 mg/lb), pantothenic acid (4 mg/lb), riboflavin (12 mg/lb), inositol (1 gm/lb), thiamine (1.5 mg/lb), folic acid (0.5 mg/lb), and the like.

Chemicals used in the present compositions can be obtained from a variety of commercial sources, including Spectrum Quality Products, Inc (Gardena, Calif.), Seltzer Chemicals, Inc., (Carlsbad, Calif.) and Jarchem Industries, Inc., (Newark, N.J.).

The active agents are combined with a carrier that is physiologically compatible with oral administration. That is, the carrier is preferably substantially inactive except for surfactant properties used in making a suspension of the active ingredients. The compositions may include other physiologically active constituents that do not interfere with the efficacy of the active agents in the composition.

Specifically, probiotic lactic acid bacterium include viable bacteria or spores (cumulatively referred to as "colony forming units") that can be ingested to form part of the gut microflora of an infant (generally two week to six month old).

A typical therapeutic compostion will contain in a one gram dosage formulation from $10^{13}$ to $10^{12}$, preferably $2\times10^5$ to $10^{10}$, colony forming units (CFU) of viable lactic acid bacterium (i.e., vegetative cell) or bacterial spore. In one preferred embodiment a therapeutic composition may include from about 10 milligrams (mg) to one gram of a bifidogenic oligosaccharide, preferably a fructooligosaccharide. The formulation may be completed in weight using any of a variety of carriers and/or binders. A preferred carrier is micro-crystalline cellose (MCC) added in an amount sufficient to complete the one gram dosage total weight. Particularly preferred formulations for a therapeutic composition of this invention are described in the Examples.

In a related embodiment, the invention contemplates a therapeutic composition comprising a bifidogenic oligosaccharide. The composition typically contains a lactic acid bacterium growth-promoting amount of the bifidogenic oligosaccharide, which growth-promoting amount can vary widely and be readily measured by growth assays as described herein. The composition will typically contain 10 mg to 1 gm of bifidogenic oligosaccharide per gram of composition depending on the dosage, route of administration and intended usage.

Carriers can be solid-based dry materials for formulations in powdered form, and can be liquid or gel-based materials for formulations in liquid or gel forms, which forms depend, in part, upon the routes or modes of administration.

Typical carriers for dry formulations include trehalose, malto-dextrin, rice flour, micro-crystalline cellulose (MCC), magnesium sterate, inositol, FOS, gluco-oligosaccharides (GOS), dextrose, sucrose, talc, and the like carriers.

Where the composition is dry and includes evaporated oils that produce a tendency for the composition to cake (adherence of the component spores, salts, powders and oils), it is preferred to include dry fillers which distribute the components and prevent caking. Exemplary anti-caking agents include MCC, talc, diatomaceous earth, amorphous silica and the like, typically added in an amount of from about 1 to 95% by weight.

Dry formulations that are rehydrated (e.g., infant formula, fruit flavored drink mix) or given to the infant in the dry state (e.g., chewable wafers, teething tablets) are preferred to hydrated formulations. Dry formulations (e.g., powders) may be added to supplement commercially available foods (e.g., infant formulas, strained prepared foods, ice cream or ice milk). The type of formulation appropriate for the infant will be readily determined by the parent or care-giver, but generally liquid formulations (e.g, electrolyte compositions and infant formula) are suitable for younger infants (about four months of age or less) and solid formulations are suitable for older infants (about four to six months or older). For compositions that are given to an infant in liquid form, the *B. coagulans* spores are preferably included in infant formula, infant food or food supplement, infant rehydration and electrolyte maintenance compositions and similar types of compositions that are rehydrated before use. These may be heated (up to about 55° C.) and cooled before use.

The carrier is preferably a formulation in which, for example, *B. coagulans* can be suspended, more preferably for hydration by the user before it is fed to the infant. For example, the formulation may be any standard powdered infant formula in which *B. coagulans* spores are mixed and suspended, which is then prepared (hydrated) before use. Similarly, *B. coagulans* spores may be suspended in a powdered rehydration formulation that includes glucose, potassium citrate, sodium chloride and/or sodium citrate to which water is added before use to produce a solution containing, for example, about $5\times10^5$ to $5\times10^7$ CFU of bacteria/l, 45 to 75 mEq/l of sodium, 20 mEqA of potassium, 35 to 65 mEq/l of chloride, 30 mEq/l of citrate and 25 g/l of glucose.

Suitable liquid or gel-based carriers are well known in the art, such as water and physiological salt solutions, urea, alcohols and glycols such as methanol, ethanol, propanol, butanol, ethylene glycol and propylene glycol, and the like. Preferably, water-based carriers are about neutral pH.

Suitable liquid carriers are well known in the art, such as water, fruit juice, glucose or fructose solutions, physiological electrolyte solutions, and the like, which may be stored refrigerated or frozen (e.g., as frozen popsicles). Preferably, water-based carriers are about neutral pH. The compositions may also include natural or synthetic flavorings and food-quality coloring agents, all of which must be compatible with maintaining viability of the lactic acid bacterium. Well known thickening agents may be added to the compositions such as corn starch, guar gum, xanthan gum and the like.

Where a liquid-based composition containing spores is provided, it is desirable to include a spore germination inhibitor to promote long term storage. Any inhibitor can be used, and therefore the invention is not to be construed as limiting. Typical and preferred inhibitors include hypersaline carriers, methylparaben, guargum, polysorbates, preservatives, and the like germination inhibitors well known in the art.

Suitable carriers include aqueous and oleaginous carries such as, for example, white petrolatum, isopropyl myristate, lanolin or lanolin alcohols, mineral oil, fragrant or essential oil, nasturtium extract oil, sorbitan mono-oleate, propylene glycol, cetylstearyl alcohol (together or in various combinations), hydroxypropyl cellulose (MW=100,000 to 1,000,000), detergents (e.g., polyoxyl stearate or sodium lauryl sulfate) and mixed with water to form a lotion, gel, cream or semi-solid composition. Other suitable carriers comprise water-in-oil or oil-in-water emulsions and mixtures of emulsifiers and emollients with solvents such as sucrose stearate, sucrose cocoate, sucrose distearate, mineral oil, propylene glycol, 2-ethyl-1,3-hexanediol, polyoxypropylene-15-stearyl ether and water. For example, emulsions containing water, glycerol stearate, glycerin, mineral oil, synthetic spermaceti, cetyl alcohol, butylparaben, propylparaben and methylparaben are commercially available. Preservatives may also be included in the carrier including methylparaben, propylparaben, benzyl alcohol and ethylene diamine tetraacetate salts. Well-known flavorings and/or colorants may also be included in the carrier. The composition may also include a plasticizer such as glycerol or polyethylene glycol (MW=800 to 20,000). The composition of the carrier can be varied so long as it does not interfere significantly with the pharmacological activity of the active ingredients or the viability of the lactic acid bacterium or *Bacillus* spores.

A therapeutic composition can be formulated to be suitable for oral administration in a variety of ways, for example in a liquid, a powdered food supplement, a solid food, a packaged foor, a wafer, and the like as described in more detail in the Examples. Other formulations will be readily apparent to one skilled in the art.

D. Therapeutic Methods for Treating Bacterial Infections

The present invention contemplates a method for treating, reducing or controlling gastrointestinal bacterial infections using a therapeutic composition or therapeutic system of this invention. The disclosed methods of treatment inhibit pathogenic bacterial growth associated with gastrointestinal infections and also reduce symptoms of these pathogenic infections.

Probiotic lactic acid bacterium, particularly *B. coagulans*, are generally regarded as safe by those skilled in the art and, therefore, suitable for ingestion in food stuffs or as a food supplement The method of the present invention comprises administration of a composition containing a viable lactic acid bacteria to the gastrointestinal tract of a human or animal to treat or prevent bacterial infection. Administration is preferably made using a liquid, powder, solid food and the like formulation compatible with oral administration, all formulated to contain a therapeutic composition of this invention using methods well known in the art.

The method of the present invention includes administration of a composition containing lactic acid bacterium cells and/or spores or isolated extracellular *B. coagulans* antibiotic metabolite to a human or animal to treat or prevent symptoms associated with enterotoxin production in the gut. In particular, for human infants, the method includes administering to the infant, for example, *B. coagulans* in food or as a food supplement. Oral administration is preferably in an aqueous suspension, emulsion, powder or solid, either already formulated into a food or as a composition which is added to food by the user. Administration to the gut may also be in the form of an anal suppository (e.g., in a gel or semi-solid formulation). All such formulations are made using standard methods.

Administration of a therapeutic composition is preferably to the gut using a gel, suspension, aerosol spray, capsule, tablet, powder or semi-solid formulation (e.g., a suppository) containing a therapeutic composition of this invention, all formulated using methods well known in the art.

Administration of the compositions containing the active probiotic lactic acid bacterium effective in preventing or treating a bacterial infection generally consist of one to ten dosages of 10 mg to 10 g of a composition per dosage for one day up to one month. Administrations are generally once every twelve hours and up to once every four hours. Preferably two to four administrations of the composition per day, of about 0.1 g to 5 g per dose, for one to seven days are sufficient to prevent or treat a bacterial infection. Of course, the specific route, dosage and timing of the administration will depend, in part, on the particular pathogen and/or condition being treated and the extent of the condition.

A preferred method involves the administration of from $10^3$ to $10^{12}$ viable bacteria or spore per day, preferably from $10^5$ to $10^{10}$, and more preferably about from $5 \times 10^8$ to $10^9$ viable bacteria or spores per day. Where the condition to be treated is SIDS and the patient is an infant under 6 months old, the dosage is typically $10^3$ to $10^6$, preferably about 5,000 to $10^5$, and more preferably about 10,000 to 50,000 viable CFU of bacteria or spores per day. Where the condition to be treated is SIDS and the patient is an infant over 6 months old, the dosage is typically $10^6$ to $10^9$, preferably about 50,000 to 250,000 and more preferably about 150,000 to 200,000 viable CFU of bacteria or spores per day.

In addition, the invention contemplates a method that comprises oral administration of a composition that contains from 10 mgs to 20 gms of a bifidogenic oligosaccharide, preferably a fructooligosaccharide, per day, preferably about 50 mg-10 gm, and more preferably about from 150 mgs to 5 gms per day, to promote growth of the probiotic lactic acid bacterium preferentially over the growth of the pathogen. The method can be combined with treatment methods using a probiotic lactic acid bacterium as described herein.

Specific methods for treating a bacterial infection are described in the Examples, and include sudden infant distress syndrome (SIDS), and the like.

E. Therapeutic Systems for Treating Bacterial Infections

The invention further contemplates a therapeutic system for treating, reducing and/or controlling bacterial infections comprising a container comprising a label and a therapeutic composition according to the present invention, wherein said label comprises instructions for use of the composition for treating said infection.

Typically, the system is present in the form of a package containing a therapeutic composition of this invention, or in combination with packaging material. The packaging material includes a label or instructions for use of the components of the package. The instructions indicate the contemplated use of the packaged component as described herein for the methods or compositions of the invention.

For example, a system can comprise one or more unit dosages of a therapeutic composition according to the invention. Alternatively, the system can contain bulk quantities of a therapeutic composition. The label contains instructions for using the therapeutic composition in either unit dose or in bulk forms as appropriate, and may include information regarding storage of the composition, disease indications, dosages, routes and modes of administration and the like information.

Furthermore, depending upon the particular contemplated use, the system may optionally contain either combined or in separate packages one or more of the following components: bifidogenic oligosaccharides, flavorings, carriers, and the like components. One particularly preferred system comprises unit dose packages of *Bacillus* spores for use in combination with a conventional infant liquid formula product, together with instructions for combining the probiotic with the formula for use in a therapeutic method.

Unless defined otherwise, all scientific and technical terms used herein have the same meaning as commonly understood by those skilled in the relevant art. Unless mentioned otherwise, the techniques employed or contemplated herein are standard methodologies well known to one of ordinary skill in the art. The examples of embodiments are for illustration only.

Throughout the specification and the claims that follow, unless the context requires otherwise, the term "comprise" and its variations, will be understood to have an inclusive meaning of any stated element, but not the exclusion of unstated elements.

EXAMPLES

The following examples relating to this invention are illustrative and should not, of course, be construed as specifically limiting the invention. Moreover, such variations of the invention, now known or later developed, which would be within the purview of one skilled in the art are to be considered to fall within the scope of the present invention hereinafter claimed.

Example 1

Preparation of *B. Coagulans* Cultures

*B. coagulans* Hammer bacteria (ATCC# 31284) was inoculated and grown to a cell density of about $10^8$-$10^9$ cells/ml in nutrient broth containing 5 g Peptone, 3 g Meat extract, 10-30 mg $MnSO_4$ and 1,000 ml distilled water, adjusted to pH 7.0, using a standard airlift fermentation vessel at 30° C. The range of $MnSO_4$ acceptable for sporulation is 1 mg/l to 1 g/l. The vegetative cells can actively reproduce up to 65° C., and the spores are stable up to 90° C. After fermentation, the *B. coagulans* Hammer bacterial cells or spores are collected using standard methods (e.g., filtration, centrifugation) and the collected cells and spores can be lyophilized, spray dried, air dried or frozen. As described herein, the supernatant from the cell culture can be collected and used as an extracellular agent secreted by *B. coagulans* which has antimicrobial activity useful in a formulation of this invention.

A typical yield from the above culture is in the range of about $10^9$-$10^{13}$ viable spores and more typically about 100 to 150 billion cells/spores per gram before drying. Spores maintain at least 90% viability after drying when stored at room temperature for up to seven years, and thus the effective shelf life of a composition containing *B. coagulans* Hammer spores at room temperature is about 10 years.

Example 2

Preparation of *B. Coagulans* Spores

A culture of dried *B. coagulans* spores was alternately prepared as follows. Ten million spores were innoculated into a one liter culture containing 24 gms potato dextrose broth, 10 gms of enzymic digest of poultry and fish tissue, 5 gms of FOS and 10 gms $MnSO_4$. The culture was maintained for 72 hours under a high oxygen environment at 37 degrees Centigrade to produce culture having about 150 billion cells per gram of culture. Thereafter, the culture was filtered to remove culture medium liquid, and the bacterial pellet was resuspended in water and freeze-dried. The freeze-dried powder is then ground to a fine powder using standard good manufacturing practice (GMP).

Example 3

Preparation of *B. Coagulans* Extracellular Products

A one liter culture of *B. coagulans* was prepared as described in Example 1. The culture was maintained for 5 days as described, at which time FOS was added at 5 gm/liter, and the culture was continued. 20 ml of carrot pulp was then added at day 7, and the culture was harvested when the culture became saturated (no substantial cell division). The culture was first autoclaved for 30 minutes at 250 degrees Farenheight, and then centrifuged at 4000 rpm for 15 min. The resulting supernatant was collected and filtered in a Buchner funnel through a 0.8 micron (u) filter, and the filtrate (pass through) was collected and further filtered through a 0.2 u Nalge vacuum filter. The resulting passthrough was collected (about 900 milliliters) to form a liquid containing an extracellular product, and used in inhibition studies.

Following the assay described in Example 4, except using *Candida albicans*, one milliliter of the above-produced extracellular product was added to the test plate in place of live *B. coagulans*. After the same culturing time, a zone of inhibition of about 10 to 25 millimeters was observed, indicating a potent antimicrobial activity of "excellent" quality, using the terminology of Example 4.

Example 4

Antimicrobial Activity of *B. coagulans*

The ability of *B. coagulans* to inhibit bacterial pathogens was demonstrated using an in vitro assay. The assay is part of a standard bacterial pathogen screen (U.S. Food and Drug Administration) and is commercially available on solid support disks (DIFCO® BACTROL® disk set). In the assay, potato-dextrose plates (DIFCO®) were prepared using standard procedures and were inoculated individually with a confluent bed $1.5 \times 10^6$ of each species of bacteria tested. Inhibition by *B. coagulans* was tested by placing on the plate about 1.5×10⁶ CFU in 10 μl of broth or buffer, plated directly in the center of the potato-dextrose plate with one test locus of about 8 mm in diameter per plate. A minimum of three test loci were used for each assay. The negative control was a 10 μl drop of a sterile saline solution and the positive control was a 10 μl volume of glutaraldehyde. The plates were then incubated for about 18 hr at 30° C. when the zone of inhibition was measured. As used herein, "excellent inhibition" means the zone was 10 mm or greater in diameter; and "good inhibition" means the zone was greater than 2 mm in diameter but less than 10 mm in diameter.

No inhibition was seen with the negative control and excellent inhibition (about 16.2 mm diameter, average of three tests) was seen with the positive control. For the enteric organisms tested, *Clostridium species* and *E. coli*, excellent inhibition by *B. coagulans* was seen. For the *Clostridium species*, *C. perfringens*, *C. difficile*, *C. botulinum*, *C. tributrycum* and *C. sporogenes*, the zone of inhibition was consistently greater than 15 mm in diameter. Similarly, excellent inhibition was also seen for the opportunistic pathogens *Pseudomonas aeruginosa* and *Staphylococcus aereus*.

Example 5

*B. coagulans* in Oral Electrolyte Maintenance Solution

An oral electrolyte maintenance powder is formulated to contain sodium chloride, potassium citrate, citric acid, glucose and powdered *B. coagulans* spores (prepared substantially as described in Example 2) to be rehydrated with sterile or boiled (and cooled) water. After rehydration, the final concentrations are: 45 to 75 mEq/l of sodium, 20 mEq/l of potassium, 35 to 65 mEq/l of chloride, 30 mEq/l of citrate, 20-25 μl of glucose and 5×10⁵ to 5×10⁷ spores/l. Flavoring (e.g., cherry, orange, grape or bubble gum flavor) may be included using standard commercially-available flavorings. The powdered formulation is packaged preferably for rehydration to one fluid liter or in individual aliquots (e.g., individual packets for rehydration to 100 ml). The powdered formula is stored dry at room temperature until it is rehydrated. The rehydrated solution is stored refrigerated for up to one week. The rehydrated solution may also be frozen into cubes or popsicles and stored at −5° C. to −20° C. for up to six months.

Example 6

*B. coagulans* in an Inert Carrier as a Food Supplement

Freeze dried *B. coagulans* (prepared substantially as described in Example 1) is mixed thoroughly with an inert carrier in powdered form (e.g., rice maltodextrin, sorbitol, gelatin, powdered rolled oats, corn starch and the like, or a combination of carriers) to form a suspension having a final concentration of about 10⁵ to 10⁸ spores/g. The powdered suspension is added to water, milk, infant formula, fruit juice or similar liquids at about 0.1-0.5 g/100 ml and mixed before providing to the infant orally.

Example 7

*B. coagulans* in a Solid Wafer Formulation

Freeze dried *B. coagulans* (prepared substantially as described in Example 1) was mixed thoroughly with a wheat or oat-based mixture (wheat or oat flour containing water and optionally sodium chloride, glucose and/or sodium bicarbonate and preservatives) to a final concentration of about 10⁶ to 10⁹ spores/g. The mixture is pressed into thin wafers of about 0.1 g each and dried or baked at about 50° C. for about 1-10 min to produce a relatively dry wafer that is stored at room temperature for up to one year. In an alternative formulation, the above mixture further contains 150 international units (IU) of lactase per wafer. Flavorings such as raspberry or orange are added to taste.

Example 8

Efficacy of *B. coagulans* Spores in Animal Model of SIDS

Experimental New Zealand white rabbits (1-3 kg) are provided with *B. coagulans* spores in their water supply at a concentration of 10³ spores/ml for one week under standard laboratory animal conditions (food and water at will for days −7 to −1). Positive control animals receive food and water (without *B. coagulans* spores) for the same period. At day 0, experimental rabbits are injected i.p. with 5 ml of a physiological buffered salt solution containing 10⁸-10⁹ *C. perfringens* Type A cells (Group I) or 10⁸-10⁹ *C. difficile* cells (Group II), and experimental control rabbits (Group III) are mock injected i.p. with 5 ml of a sterile physiological buffered salt solution. Positive control animals are similarly injected i. p.: Group IV with 10⁸-10⁹ *C. perfringens* Type A cells, Group V with 10⁸-10⁹ *C. difficile* cells, and Group VI are mock injected. Each group contains 10 rabbits. All of the rabbits continue to receive normal laboratory care and water containing 10³ *B. coagulans* spores/ml (for Groups I-III) or without spores (Groups IV-VI). After injection at day 0, the animals are monitored hourly for behavior (lethargy), breathing and heart rate for the next three days (days 1-3). The Group m control animals all remain normal for all parameters for the entire period. Group I animals generally appear to be lethargic beginning about 2-3 hr after injection. Some of the Group I animals exhibit shallow breathing and decreased heart by 4-6 hr post-injection and quietly die at 6 hr and 7 hr post-injection. Group II animals appear to be lethargic beginning about 2-3 hr after injection but recover and appear to be normal for all parameters by 4-6 hr post-injection until the end of the monitoring period at day 3. Group III and group VI animals appear to be normal for all of days 1-3. Group IV and V animals all appear to be lethargic about 1-3 hr post-injection, with decreasing breathing and heart rate until death at 2-6 hr post-injection.

Thus, in this animal model, oral administration of *B. coagulans* spores significantly prevents SIDS symptoms and death of the animals injected with *C. perfringens* or *C. difficile*.

Example 9

Treatment of Infant Botulism with Orally Administered *B. coagulans*

Infants aged 3 weeks to 6 months who are admitted to a medical facility with intestinal disorders having any of a variety of symptoms (vomiting, diarrhea, lethargy or flaccid paralysis, poor appetite, shallow breathing, fever) are tested for presence of botulinum toxin using the mouse toxin neutralization test (Amon S. S. et al., *Lancet* 1: 1273-1277, 1978). The infants are treated with oral rehydration using an oral electrolyte maintenance powder dissolved in sterile water substantially as described in Example 5. Upon admittance, samples from the infants are tested to determine if a heat-labile substance that can be neutralized with antitoxin specific for *C. botulinum* Type A toxin is present. Briefly, undiluted serum or a buffer extract of colon contents obtained from each infant are divided into aliquots and one aliquot is heated to 100° C. for 10 min, one aliquot is untreated, and a third aliquot is treated with trypsin to increase toxicity. The three aliquot (about 0.5 ml each) are injected i.p. into mice, which died within 24 hr if *C. botulinum* Type A toxin is present. For those samples which tested positive for heat-labile toxin, the presence of *C. botulinum* Type A toxin is confirmed by repeating the assay using antitoxin-neutralized samples (which do not kill the mice). At days two and three of treatment, fecal or colon contents samples are tested for *C. botulinum* Type A toxin using the same assay.

Infants are given the oral electrolyte maintenance solution containing *B. coagulans* at about $5\times10^5$ spores/l as soon as possible after admittance and during the first 4-6 hr of admittance. Infants are provided with the oral electrolyte maintenance solution as follows. Infants up to 5 kg (11-12 lb) are given about 200-250 ml of the oral electrolyte maintenance solution; infants of about 6 kg (12-15 lb) are given about 300-350 ml; infants of about 8 kg (15-20 lb) are given about 400-450 ml; and infants of about 10 kg (20-25 lb) or more are given about 500 ml. Thereafter, during the first 24 hr of admittance infants are orally rehydrated as needed as determined by the treating physician. During the 2-7 days following admittance, the infants are given sufficient oral electrolyte maintenance solution containing *B. coagulans* spores to administer about $5\times10^5$ spores/day.

Infants having confirmed infant botulism upon admittance respond positively to oral rehydration and none show evidence of *C. botulinum* Type A toxin in fecal or colon contents samples collected after one or two days of treatment.

Example 10

Efficacy of *B. coagulans* in Preventing SIDS in Human Infants

Because SIDS does not present symptoms in advance, a human study of prevention of SIDS relies on statistical analysis of human infants. At the beginning of the study, two groups of 500 infants each, at risk of SIDS because of maternal smoking, are followed by regular medical check-ups from the ages of two weeks to eight months. Group I is given a daily dose of *B. coagulans* spores in water or infant formula (110 spores for infants of two weeks to two months old, $10^6$ spores for infants of nine weeks to six months old, and a weekly dose of $10^7$ spores for infants over six months old to eight months old). Group II, the age-matched controls, are given substantially the same amounts of water and infant formula (i.e., normal nutritional requirements, without *B. coagulans* spores). Another control group (Group III) includes any infants who are not included in Groups I or II but, during the course of the study, die with SIDS and are necropsied at the same medical facility. This third group is age-matched to the infants initially included in the study, but includes infants between 1-5 months of age.

During the course of the study, fecal samples are collected and analyzed weekly and serum samples are collected and analyzed monthly for Groups I and II. For Group III, fecal and serum samples are obtained as soon as possible during necropsy and analyzed thereafter. All samples are stored at −20° C. until analyzed if they are not analyzed within one hr of collection and are stored on ice (0° C.) if not frozen upon collection. Serum samples are analyzed for the presence of heat labile toxin (substantially as described in Example 6), and for toxins from *C. perfringens*, *C. difficile*, *C. botulinum* and *S. aureus* using immunoassays substantially as previously described (Murrell W. G et al., *J. Med. Microbiol.* 39:114-127, 1993). Bacterial detection and enumeration of fecal samples are performed using standard methods (*Bergey's Manual of Systemic Bacteriology*, Vol. 1-2, Sneath, P. H. A. et al., eds., Williams & Wilkins, Baltimore, Md., 1986) and substantially as previously described (Murrell W. G et al., *J. Med. Microbiol.* 39:114-127, 1993). Heat labile toxin is fecal samples is determined substantially as described in Example 9.

Infants in Group II correspond roughly to the age-matched controls reported by Murrell W. G et al. (*J. Med. Microbiol.* 39:114-127, 1993) and have similar incidence of SIDS-associated bacterial infections and toxins. The Group II infants are a larger sample size than the age-matched controls reported by Murrell W. G et al. (*J. Med Microbiol.* 39:114-127, 1993) and are at higher risk of SIDS due to maternal smoking and, therefore, are expected to have a somewhat higher incidence of SIDS-associated bacterial infections and toxins. Infants in Group II that show symptoms of gastrointestinal infection and have confirmed presence of SIDS-associated bacteria in fecal or colon-contents samples (*C. perfringens*, *C. difficile*, *C. botulinum* or *S. aureus*) are immediately withdrawn from the control Group II and administered an oral electrolyte maintenance solution containing *B. coagulans* spores, substantially as described in Example 9. Thereafter, these treated infants continue to be administered foods or liquids containing *B. coagulans* spores and are included in Group I infants.

Infants in Group I survive the entire testing period and have significantly fewer symptoms of gastrointestinal infections compared to Group II. Bacterial counts in fecal samples from Group I infants are significantly fewer for *C. perfringens*, *C. difficile*, *C. botulinum* and *S. aureus* compared to group II.

The Group III infants (SIDS victims) show significantly higher frequency of gastrointestinal infection with *C. perfringens*, *C. difficile*, *C. botulinum* or *S. aureus* and significantly higher frequency of serum toxins than infants in either Group I or Group II. Thus, although Group I infants would be expected to have at least one death due to SIDS during the test period, the *B. coagulans* probiotic appears to have effectively prevented SIDS and to have significantly reduced the frequency at which SIDS-associated bacteria or their toxins are detected.

The invention has been described in the above examples using a variety of formulations, although it should be apparent that various other carrier agents that are compatible with the probiotic compositions may be substituted in the examples to give similar results. Accordingly, the invention may be embodied in other specific forms without departing from it in spirit. The examples are to be considered in all respects only as illustrative and not as restrictive, and the scope of the invention is indicated by the claims that follow. All modifications which come within the meaning and range of the lawful equivalency of the claims are to be embraced within their scope.

What is claimed is:

1. A method of reducing a bacterial gastrointestinal infection in a human, said bacterial gastrointestinal infection selected from the group consisting of *Clostridium perfringens*, *Clostridium difficile*, *Clostridium botulinum*,

*Clostridium tributrycum, Clostridium sporogenes, Escherichia coli, Pseudomonas aeruginosa*, and *Staphylococcus aureus*, comprising the steps of:

a) orally administering to a human subject in need thereof a composition comprising:
   i.) viable colony forming units (CFU) of a non-pathogenic lactic acid bacteria, wherein said non-pathogenic lactic acid bacteria is *Bacillus coagulans*; and
   ii) an oral electrolyte maintenance formulation; and b) allowing said non-pathogenic lactic acid bacteria to grow in the human subject's gastrointestinal tract, thereby reducing a bacterial gastrointestinal infection.

2. The method of claim 1, wherein the human subject is an infant at risk for Sudden Infant Death Syndrome (SIDS).

3. The method of claim 1, wherein the non-pathogenic lactic acid bacteria is included in the composition in the form of spores.

4. The method composition of claim 1, wherein the non-pathogenic lactic acid bacteria is included in the composition in the form of a dried cell mass.

5. The method of claim 1, wherein the non-pathogenic lactic acid bacteria is in the form of spores, and said method further comprises allowing the spores to germinate after the administering step.

6. The method of claim 1, wherein said composition contains $10^3$ to $10^{12}$ CFU of viable non-pathogenic lactic acid bacteria or spores per gram of composition.

7. The method of claim 1, wherein said administering comprises introducing into the digestive tract from 0.1 to 50 grams per day of the non-pathogenic lactic acid bacteria in step (a)(i).

8. The method of claim 1, wherein said administering comprises introducing into the digestive tract from $10^2$ to $10^{10}$ viable bacteria or spores per day.

9. The method of claim 8, wherein said administering comprises introducing into the digestive tract from $10^3$ to $10^6$ viable bacteria or spores per day.

10. The method of claim 8, wherein said administering comprises introducing into the digestive tract from $10^6$ to $10^9$ viable bacteria or spores per day.

11. The method of claim 1, wherein said composition in step (a) further comprises an effective amount of a bifidogenic oligosaccharide to promote the growth of the non-pathogenic lactic acid bacteria.

12. The method of claim 11, wherein the bifidogenic oligosaccharide is selected from the group consisting of fructo-oligosaccharide (FOS), gluco-oligosaccharide (GOS), raffinose, and long-chain oligosaccharides.

13. The method of claim 12, wherein the bifidogenic oligosaccharide comprises a polysaccharide having a polymer chain length of about 4 to 100 sugar units.

14. The method of claim 1, wherein the composition further comprises about 10 milligrams to about 1 gram of FOS per gram of composition.

15. The method of claim 1, wherein the composition further comprises from 100 to 500 milligrams of FOS per gram of composition.

16. The method of claim 1, wherein the administering comprises introducing into the digestive tract from 10 milligrams to 20 grams of fructo-oligosaccharide per day.

17. The method of claim 1, wherein the administering comprises introducing into the digestive tract from 150 milligrams to 5 grams of fructo-oligosaccharide per day.

18. The method of claim 1, wherein the composition in step (a) further comprises a food substance, flavoring, vitamin or mineral.

19. The method of claim 1 wherein the oral electrolyte maintenance formulation in step (a)(ii) is a powder comprising sodium chloride, potassium citrate, citric acid, or glucose.

20. The method of claim 1 wherein the oral electrolyte maintenance formulation in step (a)(ii) is rehydrated with water to produce a solution comprising 45 to 75 mEq/l of sodium, 20 mEq/l of potassium, 35 to 65 mEq/l of chloride, 30 mEq/l of citrate, 20-25 g/l of glucose, and wherein said non-pathogenic lactic acid bacteria in step (a)(i) comprises about $5\times10^5$ to about $5\times10^7$ viable CFU of said bacteria/l.

21. The method of claim 1, wherein the composition in step (a) further comprises an extracellular product of *Bacillus coagulans*.

22. The method of claim 21, wherein the extracellular product is a supernatant or filtrate of a culture of an isolated *Bacillus coagulans* strain.

23. The method of claim 1, wherein the non-pathogenic lactic acid bacteria comprises *Bacillus coagulans* hammer strain Accession No. ATCC 31284.

24. The method of claim 1, wherein the oral electrolyte maintenance formulation in step (a)(ii) comprises 45 to 75 mEq/l of sodium, 20 mEq/l of potassium, 35 to 65 mEq/l of chloride, 30 mEq/l of citrate, and 20 to 25 g/l of glucose.

* * * * *